US011266759B2

(12) United States Patent
Barber, III (10) Patent No.: US 11,266,759 B2
(45) Date of Patent: Mar. 8, 2022

(54) ILLUMINATOR WITH ULTRAVIOLET AND BLUE-ULTRAVIOLET LIGHT SOURCE

(71) Applicant: Sensor Electronic Technology, Inc., Columbia, SC (US)

(72) Inventor: Arthur Peter Barber, III, Lexington, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 0 days.

(21) Appl. No.: 16/878,509

(22) Filed: May 19, 2020

(65) Prior Publication Data

US 2020/0276345 A1 Sep. 3, 2020

Related U.S. Application Data

(63) Continuation of application No. 16/170,617, filed on Oct. 25, 2018, now Pat. No. 10,688,211.

(Continued)

(51) Int. Cl.
*A61L 2/10* (2006.01)
*A61L 2/24* (2006.01)
(Continued)

(52) U.S. Cl.
CPC .............. *A61L 2/24* (2013.01); *A61L 2/0047* (2013.01); *A61L 2/0052* (2013.01); *A61L 2/084* (2013.01); *A61L 2/088* (2013.01); *A61L 2/10* (2013.01); *A61N 5/0624* (2013.01); *G01N 21/6447* (2013.01); *G01N 21/6456* (2013.01);
(Continued)

(58) Field of Classification Search
CPC ........ A61L 2/24; A61L 2/0047; A61L 2/0052; A61L 2/084; A61L 2/088
See application file for complete search history.

(56) References Cited

U.S. PATENT DOCUMENTS 7,553,456 B2 6/2009 Gaska et al.
7,634,996 B2 12/2009 Gaska et al.
(Continued)

FOREIGN PATENT DOCUMENTS

KR 20130125436 A 11/2013
KR 10-1704502 B1 2/2017

OTHER PUBLICATIONS

Maupin, H. H., U.S. Appl. No. 16/170,617, Notice of Allowance, dated Feb. 20, 2020, 9 pages.
(Continued)

*Primary Examiner* — Hugh Maupin
(74) *Attorney, Agent, or Firm* — LaBatt, LLC (57) ABSTRACT

An illuminator comprising more than one set of ultraviolet radiation sources. A first set of ultraviolet radiation sources operate in a wavelength range of approximately 270 nanometers to approximately 290 nanometers. A second set of ultraviolet radiation sources operate in a wavelength range of approximately 380 nanometers to approximately 420 nanometers. The illuminator can also include a set of sensors for acquiring data regarding at least one object to be irradiated by the first and the second set of ultraviolet radiation sources. A control system configured to control and adjust a set of radiation settings for the first and the second set of ultraviolet radiation sources based on the data acquired by the set of sensors.

21 Claims, 4 Drawing Sheets

Related U.S. Application Data (60) Provisional application No. 62/576,695, filed on Oct. 25, 2017.

(51) Int. Cl.
  *G01N 21/64* (2006.01)
  *A61L 2/08* (2006.01)
  *A61N 5/06* (2006.01)
  *A61L 2/00* (2006.01)

(52) U.S. Cl.
  CPC ...... *A61L 2202/11* (2013.01); *A61L 2202/122* (2013.01); *A61L 2202/14* (2013.01); *A61L 2202/24* (2013.01); *A61N 2005/0626* (2013.01); *A61N 2005/0661* (2013.01); *A61N 2005/0662* (2013.01)

(56) References Cited

U.S. PATENT DOCUMENTS

| | | |
|---|---|---|
| 8,277,734 B2 | 10/2012 | Koudymov et al. |
| 8,980,178 B2 | 3/2015 | Gaska et al. |
| 9,006,680 B2 | 4/2015 | Bettles et al. |
| 9,034,271 B2 | 5/2015 | Shur et al. |
| 9,061,082 B2 | 6/2015 | Gaska et al. |
| 9,138,499 B2 | 9/2015 | Bettles et al. |
| 9,179,703 B2 | 11/2015 | Shur et al. |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |
| 9,724,441 B2 | 8/2017 | Shur et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Bettles et al. |
| 9,802,840 B2 | 10/2017 | Shturm et al. |
| 9,878,061 B2 | 1/2018 | Shur et al. |
| 9,919,068 B2 | 3/2018 | Shur et al. |
| 9,974,877 B2 | 5/2018 | Bettles et al. |
| 9,981,051 B2 | 5/2018 | Shur et al. |
| 9,987,383 B2 | 6/2018 | Bilenko et al. |
| 9,999,782 B2 | 6/2018 | Shur et al. |
| 10,004,821 B2 | 6/2018 | Dobrinsky et al. |
| 10,040,699 B2 | 8/2018 | Smetona et al. |
| 10,099,944 B2 | 10/2018 | Smetona et al. |
| 10,166,307 B2 | 1/2019 | Dobrinsky et al. |
| 10,433,493 B2 | 10/2019 | Barber, III et al. |
| 2009/0272029 A1 | 11/2009 | Aiking et al. |
| 2009/0314308 A1 | 12/2009 | Kim et al. |
| 2011/0278467 A1 | 11/2011 | Tanaka |
| 2012/0051030 A1 | 3/2012 | Johnson |
| 2012/0223216 A1* | 9/2012 | Flaherty ............... A61L 2/10 250/214.1 |
| 2013/0048545 A1 | 2/2013 | Shatalov et al. |
| 2014/0060104 A1 | 3/2014 | Shur et al. |
| 2014/0061509 A1 | 3/2014 | Shur et al. |
| 2014/0116079 A1 | 5/2014 | Murphy et al. |
| 2014/0119985 A1 | 5/2014 | Berg et al. |
| 2014/0202962 A1 | 7/2014 | Bilenko et al. |
| 2015/0165079 A1 | 6/2015 | Shur et al. |
| 2016/0000951 A1 | 1/2016 | Kreiner et al. |
| 2016/0114186 A1 | 4/2016 | Dobrinsky et al. |
| 2017/0057842 A1 | 3/2017 | Dobrinsky et al. |
| 2017/0100495 A1 | 4/2017 | Shur et al. |
| 2017/0189711 A1 | 7/2017 | Shur et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2017/0290934 A1 | 10/2017 | Dobrinsky et al. |
| 2017/0368215 A1 | 12/2017 | Shatalov et al. |
| 2018/0028700 A1 | 2/2018 | Dobrinsky et al. |
| 2018/0092308 A1 | 4/2018 | Barber et al. |
| 2018/0104368 A1 | 4/2018 | Dobrinskly et al. |
| 2018/0113066 A1 | 4/2018 | Freitag et al. |
| 2018/0117194 A1 | 5/2018 | Dobrinsky et al. |
| 2018/0185529 A1 | 7/2018 | Shur et al. |
| 2018/0221521 A1 | 8/2018 | Shur et al. |
| 2018/0243458 A1 | 8/2018 | Shatalov et al. |
| 2018/0339075 A1 | 11/2018 | Kennedy et al. |
| 2019/0030477 A1 | 1/2019 | Shatalov |
| 2019/0099613 A1 | 4/2019 | Estes et al. |
| 2019/0100445 A1 | 4/2019 | Dobrinsky et al. |
| 2019/0100718 A1 | 4/2019 | Estes et al. |

OTHER PUBLICATIONS

Maupin, H. H., U.S. Appl. No. 16/170,617, Office Action 1, dated Oct. 11, 2019, 15 pages.

Park, H, L., Application No. PCT/US2018/057505, Search Report and Written Opinion, dated May 3, 2019, 12 pages.

Marsano, Flavio, EP Application No. 18870125 4, Supplemental Search Report, dated Jun. 29, 2021, 7 pages.

* cited by examiner

ILLUMINATOR WITH ULTRAVIOLET AND BLUE-ULTRAVIOLET LIGHT SOURCE

REFERENCE TO RELATED APPLICATIONS

The current application is a continuation of U.S. patent application Ser. No. 16/170,617, filed on 25 Oct. 2018, which claims the benefit of U.S. Provisional Application No. 62/576,695, filed on 25 Oct. 2017, each of which is hereby incorporated by reference.

TECHNICAL FIELD

The disclosure relates generally to the illumination treatment of surfaces, and more particularly, to treating surfaces with ultraviolet (UV) and blue-UV radiation.

BACKGROUND ART

Ultraviolet radiation has been used to destroy infectious materials present within various medical facilities, such as, surgery rooms. Thus, it is known to destroy infectious material using ultraviolet radiation. While the generation of ultraviolet, type C (UV-C) radiation for the purpose of sterilization of surfaces is not a new idea, traditional hand-held products utilize mercury lights are undesirable for several reasons. These products can be difficult to maintain, contain mercury, and may require high voltages. Recently, UV-C light emitting diodes (LEDs) have appeared on the market and are capable for effective sterilization of surfaces. However, such UV-C LEDs still suffer from low efficiency.

SUMMARY OF THE INVENTION

Aspects of the invention provide an illuminator with ultraviolet and blue-UV sources. Prolonged exposure to blue-UV light, e.g., in the wavelength range of approximately 380 nanometers (nm) to approximately 420 nm, results in sterilization due to generation of reactive oxygen species (ROS). The present invention combines both UV LEDs and blue-UV LEDs in order to improve the disinfection of surfaces.

A first aspect of the invention provides an illuminator, comprising: a first set of ultraviolet radiation sources, each ultraviolet radiation source in the first set of ultraviolet radiation sources operating in a wavelength range of approximately 270 nanometers to approximately 290 nanometers; a second set of ultraviolet radiation sources, each ultraviolet radiation source in the second set of ultraviolet radiation sources operating in a wavelength range of approximately 380 nanometers to approximately 420 nanometers; a set of sensors for acquiring data regarding at least one object to be irradiated by the first and the second set of ultraviolet radiation sources; and a control system configured to control and adjust a set of radiation settings for the first and the second set of ultraviolet radiation sources based on the data acquired by the set of sensors.

A second aspect of the invention provides a system, comprising: at least one object; an illuminator configured to disinfect the at least one object by directing ultraviolet radiation at the at least one object, the illuminator comprising: a first set of ultraviolet radiation sources, each ultraviolet radiation source in the first set of ultraviolet radiation sources operating in a wavelength range of approximately 270 nanometers to approximately 290 nanometers; a second set of ultraviolet radiation sources, each ultraviolet radiation source in the second set of ultraviolet radiation sources operating in a wavelength range of approximately 380 nanometers to approximately 420 nanometers; a set of sensors for acquiring data regarding at least one object to be irradiated by the first and the second set of ultraviolet radiation sources; and a control system configured to control and adjust a set of radiation settings for the first and the second set of ultraviolet radiation sources based on the data acquired by the set of sensors.

A third aspect of the invention provides an enclosure, comprising: an illuminator located adjacent to the enclosure, the illuminator configured to direct ultraviolet radiation within the enclosure, the illuminator comprising: a first set of ultraviolet radiation sources, each ultraviolet radiation source in the first set of ultraviolet radiation sources operating in a wavelength range of approximately 270 nanometers to approximately 290 nanometers; a second set of ultraviolet radiation sources, each ultraviolet radiation source in the second set of ultraviolet radiation sources operating in a wavelength range of approximately 380 nanometers to approximately 420 nanometers; a set of sensors for acquiring data regarding at least one object to be irradiated by the first and the second set of ultraviolet radiation sources; and a control system configured to control and adjust a set of radiation settings for the first and the second set of ultraviolet radiation sources based on the data acquired by the set of sensors.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide an illuminator comprising more than one set of ultraviolet radiation sources. A first set of ultraviolet radiation sources operate in a wavelength range of approximately 270 nanometers to approximately 290 nanometers. A second set of ultraviolet radiation sources operate in a wavelength range of approximately 380 nanometers to approximately 420 nanometers. The illuminator can also include a set of sensors for acquiring data regarding at least one object to be irradiated by the first and the second set of ultraviolet radiation sources. A control system configured to control and adjust a set of radiation settings for the first and the second set of ultraviolet radiation sources based on the data acquired by the set of sensors.

Ultraviolet radiation, which can be used interchangeably with ultraviolet light, means electromagnetic radiation having a wavelength ranging from approximately 10 nanometers (nm) to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm. As used herein, blue-ultraviolet (blue-UV) radiation has a wavelength between approximately 380 nm to 420 nm.

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 260 nm to 270 nm is a preferred range for facilitating disinfection, sterilization of various objects. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure is considered to be "reflective" to ultraviolet light of a particular wavelength when the material/structure has an ultraviolet reflection coefficient of at least 30 percent for the ultraviolet light of the particular wavelength. A highly ultraviolet reflective material/structure has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through. Also, unless otherwise noted, the term "set" means one or more (i.e., at least one) and the phrase "any solution" means any now known or later developed solution.

Figure 1:
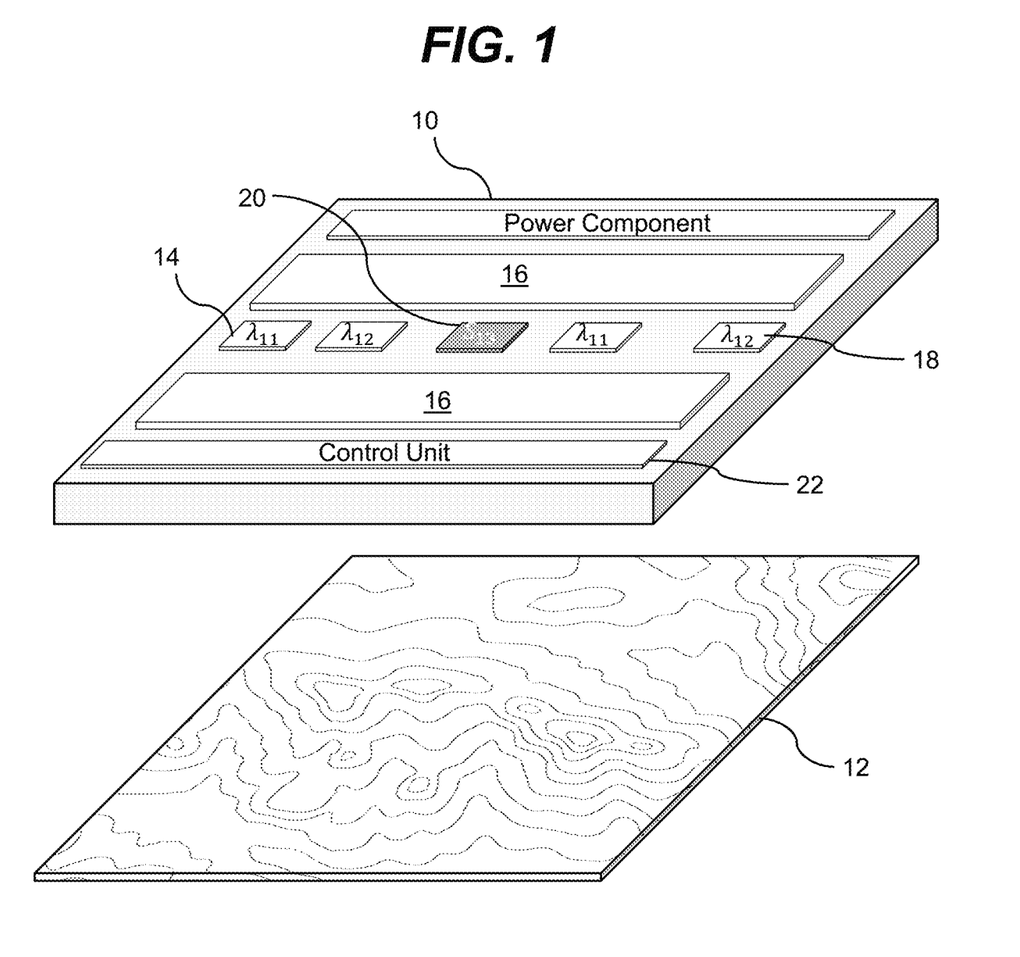
FIG. 1 shows a schematic of an illustrative illuminator according to an embodiment

Turning to the drawings, FIG. 1 shows an illustrative ultraviolet illuminator 10 according to an embodiment for irradiating an object 12 that requires disinfection. The illuminator 10 can include a first set of radiation sources 14 and a second set of radiation sources 16 for irradiating the object 12. It is understood that first and second set of radiation sources 14, 16, along with other features of the illuminator 10, can be located at any location on the surface of the illuminator 10 and the depiction in FIG. 1 is on an example of one configuration. To this extent, it is understood that the particular arrangement, sizes, quantities, etc., of the illustrative components of the illuminator 10 depicted in FIG. 1 is only illustrative of various arrangements, sizes, quantities, etc., of the components.

The first set of radiation sources 14 and the second set of radiation sources 16 can comprise any combination of one or more ultraviolet radiation emitter. Examples of an ultraviolet radiation emitter can include, but are not limited to, high intensity ultraviolet lamps (e.g., high intensity mercury lamps), discharge lamps, ultraviolet LEDs, super luminescent LEDs, laser diodes, and/or the like. In one preferred embodiment, the ultraviolet radiation source can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the ultraviolet radiation source can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures can include, but are not limited to, a wave guide, a plurality of ultraviolet fibers, each of which terminates at an opening, a diffuser, and/or the like.

The first set of radiation sources 14 can include ultraviolet radiation sources that operate in the ultraviolet wavelength range (e.g., 10 nm to 400 nm). In an embodiment, the first set of radiation sources 14 can operate to emit radiation having a peak wavelength in or immediately adjacent to the UV-C wavelength range and are referred to as "UV-C sources" herein. For example, the first set of radiation sources 14 can emit radiation having a peak wavelength in a range of approximately 250 nm to approximately 290 nm. In a more specific embodiment, the first set of radiation sources 14 can operate in the wavelength range of approximately 270 nm to approximately 290 nm. Although FIG. 1 shows two instances of the first set of radiation sources 14 on the illuminator 10, it is understood that the illuminator 10 can include any number of instances of the first set of radiation sources 14. Furthermore, each of the instances of the first set of radiation sources 14 can include any number of sources.

In an embodiment, each of the ultraviolet radiation sources in the first set of radiation sources 14 can operate at a different peak wavelength ($\lambda$). In an embodiment, each of the ultraviolet radiation sources in the first set of radiation sources 14 can irradiate a different location of the object 12. In another embodiment, the first set of radiation sources 14 can all irradiate different locations on the object 12 but with relatively uniform radiation. In another embodiment, more than one ultraviolet radiation source in the first set of ultraviolet radiation sources 14 can irradiate a single location on the object 12 but each ultraviolet radiation source can operate at a different wavelength and/or intensity.

In an embodiment, each of the ultraviolet radiation sources in the first set of radiation sources 14 can operate at a specific wavelength within the range of 250 nm to 360 nm. In an embodiment, the wavelength range can be selected to be significantly narrower, depending on the type of microorganisms being sterilized. For example, in an embodiment, the wavelength range can extend from 270 nm to 320 nm. In another embodiment, depending on the object 12, the wavelength range can extend from 280 nm to 300 nm, or from 260 nm to 280 nm. In one embodiment, the ultraviolet radiation sources can have a peak wavelength that ranges from 270 nm to 300 nm. In another embodiment, the ultraviolet radiation sources can have a peak wavelength of 295 nm with a full width half maximum of 10 nm. It is understood that these ranges are only examples and the wavelength range for the ultraviolet radiation sources in the first set of radiation sources 14 can be any wavelength range within the range of 250 nm to 360 nm.

Optical elements can be included to facilitate the efficiency of radiation. In an embodiment, the first set of radiation sources 14 can include a set of reflective optical elements in order to focus the ultraviolet radiation to specific locations on the object 12. In an embodiment, the set of reflective optical elements can include one or more of: a lens, a set of lenses, a parabolic reflector, a wave-guiding structure, and/or the like. In an embodiment, the optical elements can include UV transparent material.

In an embodiment, the second set of radiation sources 16 can include blue-UV radiation sources that operate in the blue-UV wavelength range of approximately 380 nm to approximately 420 nm. The second set of radiation sources 16 can operate at a higher intensity, with wider coverage that continuously operate over an extended period of time. For example, the second set of radiation sources 16 operating in the blue-UV wavelength range can operate continuously for several days. Prolonged exposure to radiation in the blue-UV wavelength range results in sterilization due to generation of reactive oxygen species (ROS). ROS are chemically reactive chemical species that contain oxygen. The ROS can disrupt the proliferation of microorganisms on the object 12 by binding to and oxidizing the microorganisms.

It is understood that both the first set of radiation sources 14 and the second set of radiation sources 16 can produce a distributed intensity over one or more areas of the object 12 that is located a distance away from the illuminator 10. In an embodiment, the distance between the illuminator 10 and the object 12 can range from a few centimeters to several meters. In an embodiment, irradiation of a location defines a region of the object 12 that is impinged by radiation, wherein the intensity of radiation deposited at the boundary of the region is at most 10% of the intensity of light deposited at the center of the region. It is understood that the position of irradiated locations can be adjusted to result in separate locations over the surface of the object 12, wherein separate means that the intensity of radiation between each of the locations is no larger than 10% of the intensity in the center of the locations. In addition, these locations of irradiation can be designed to have relatively uniform radiation, with radiation intensity varying through the location by no more than several times (e.g., a factor of three or less) between any two points within the location.

The illuminator 10 can also include a third set of radiation sources 18. In an embodiment, the third set of radiation sources 18 can include sources of fluorescent radiation. In an embodiment, the third set of radiation sources 18 can include visible radiation sources such as incandescent, fluorescent, laser, solid state, and/or the like radiation sources that operate at least partially in the wavelength range of 400 nm to 700 nm. For example, the third set of radiation sources 18 can include a visible source of collimated light capable of irradiating a surface of the object 12 at a set of angles. Furthermore, the illuminator can include a sensor 20 (e.g., a visual camera) capable of detecting the intensity of the reflected light at the set of angles. In an embodiment, the third set of radiation sources 18 can include infrared radiation sources such as blackbody, solid state, and/or the like radiation sources that emit radiation that is in the wavelength range of 700 nm to 1 millimeter (mm).

Although only one sensor 20 is shown on the illuminator 10, it is understood that the illuminator 10 can include any number of sensors 20. To this extent, the illuminator 10 can include one or more of various types of sensors 20. The set of sensors 20 can be configured to measure a plurality of conditions associated with the radiation from any of the sets of radiation sources 14, 16, 18 or the object 12. The set of sensors 20 can include sensors to detect visible radiation, UV radiation (e.g., blue-UV, UV-C, and/or the like), infrared radiation, chemicals fluorescence, and/or the like. For example, in an embodiment, the set of sensors 20 can include one or more sensors configured to detect fluorescent light radiated by the microorganisms on the object 12. In an embodiment, the set of sensors 20 can include one or more fluorescent radiation sensors configured to detect fluorescent radiation induced on the surface of the object 12 by one or more of the sets of radiation sources 14, 16, 18. In an embodiment, the third set of radiation sources 18 can include one or more visible radiation sources and the set of sensors 20 can include a visual camera configured to monitor the conditions of the object 12. For example, the visual camera can detect changes in the surface appearance of the object 12 (e.g., changes in color, mildew growth, presence of dirt particles, changes in reflective or scattering properties of the surface, and/or the like). In an embodiment, the set of sensors 20 can also include environmental condition sensors, such as a temperature sensor, a humidity sensor, a gas sensor, and/or the like.

In an embodiment, the object 12 can include a photo-catalyst, such as titanium dioxide ($TiO_2$), copper, silver, copper/silver particles, and/or the like. Such a photo-catalyst can further disrupt the growth and proliferation of microorganisms on the object 12.

The illuminator 10 includes a control unit 22 that is configured to control and/or adjust the set of radiation sources 14, 16, 18 and the set of sensors 20. The control unit 22 can control and/or adjust the set of radiation sources 14, 16, 18 according to a plurality of radiation settings. The plurality of radiation settings can be based upon various environmental conditions in which the object 12 is placed (e.g., the location of the object 12, and/or the like), various attributes regarding the object 12 and/or the area surrounding the object 12 determined by the set of sensors 20, and/or the like. For example, the controller 22 can determine a set of attributes regarding the object 12 and/or the area surrounding the object 12 and adjust the plurality of radiation settings of the set of radiation sources 14, 16, 18 and the set of sensors 20 to achieve a target set of attributes for the object 12 and/or the area surrounding the object 12.

Figure 2:
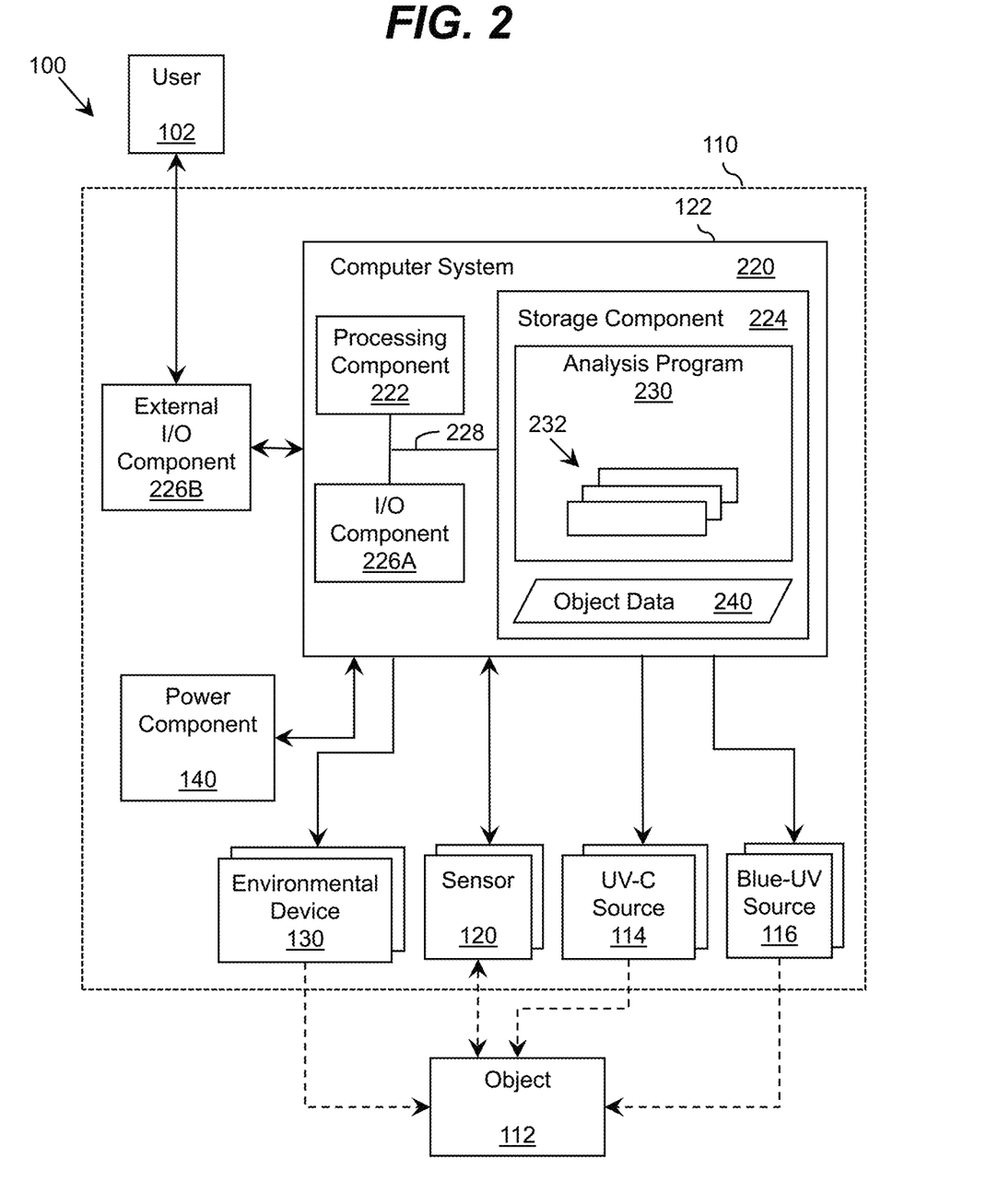
FIG. 2 shows a schematic block diagram representative of an illustrative system including an illuminator according to an embodiment.

FIG. 2 shows a schematic of an illustrative system 100 that can be implemented with any of the embodiments described in conjunction with FIG. 1 according to an embodiment. In this embodiment, the system 100 is shown including the illuminator 110 that includes the set of UV-C sources 114, the set of blue-UV sources 116, the set of sensors 120, and a set of environmental devices 130. The third set of radiation sources 118 (FIG. 1) are not shown for clarity, but it is understood that they can be included in the illuminator 110.

As discussed herein, the system 100 can include the control unit 122 for controlling and adjusting the plurality of radiation settings for the set of UV-C sources 114 and the set of blue-UV sources 116 and controlling and receiving data from the set of sensors 120. In an embodiment, the control unit 122 can be implemented as a computer system 220 including an analysis program 230, which makes the computer system 220 operable to manage the various components in the illuminator 110 in the manner described herein. In particular, the analysis program 230 can enable the computer system 220 to operate the set of UV-C sources 114 and the set of blue-UV sources 116 in order to generate and direct ultraviolet radiation towards the object 112. The computer system 220 can also process data corresponding to one or more attributes regarding the object, which can be acquired by the set of sensors 120, and/or an ultraviolet radiation history stored as object data 240. The computer system 220 can individually control each ultraviolet radiation source in the set of UV-C sources 114 and the set of blue-UV sources 116 and each individual sensor in the set of sensors 120 and/or control two or more of the ultraviolet radiation sources and the sensors as a group. Furthermore, the ultraviolet radiation sources in the illuminator 110 can emit ultraviolet radiation of substantially the same wavelength or of multiple distinct wavelengths.

In an embodiment, during an initial period of operation, the computer system 220 can acquire data from at least one of the sensors in the set of sensors 120 regarding one or more attributes of the object 112 and generate data 240 for further processing. The data 240 can include information regarding a presence of an object 112, a weight of an object 112, a microorganism concentration and/or location on the object 112, a size of an object 112, and/or the like. The computer system 220 can use the data 240 to control one or more aspects of the ultraviolet radiation generated by the set of UV-C sources 114 and/or the set of blue-UV sources 116 during an illumination period.

Furthermore, one or more aspects of the operation of the ultraviolet radiation sources in the set of UV-C sources 114 and the set of blue-UV sources 116 can be controlled or adjusted by a user 102 via an external interface I/O component 226B. The external interface I/O component 226B can be located on the exterior of the illuminator 110, and used to allow the user 102 to control (e.g., selectively turn on/off) the ultraviolet radiation sources 114, 116.

The external interface I/O component 226B can include, for example, a touch screen that can selectively display user interface controls, such as control dials, which can enable the user 102 to adjust one or more of: an intensity, scheduling, and/or other operational properties of the set of ultraviolet radiation sources 114, 116 in the illuminator 110 (e.g., operating parameters, radiation characteristics). In an embodiment, the external interface I/O component 226B could conceivably include a keyboard, a plurality of buttons, a joystick-like control mechanism, and/or the like, which can enable the user 102 to control one or more aspects of the operation of the set of ultraviolet radiation sources 114, 116. The external interface I/O component 226B also can include any combination of various output devices (e.g., an LED, a visual display), which can be operated by the computer system 220 to provide status information pertaining to the illumination period of the object for use by the user 102. For example, the external interface I/O component 226B can include one or more LEDs for emitting a visual light for the user 102, e.g., to indicate a status of the illumination period. In an embodiment, the external interface I/O component 226B can include a speaker for providing an alarm (e.g., an auditory signal), e.g., for signaling that ultraviolet radiation is being generated or that the object had been illuminated by ultraviolet radiation.

The computer system 220 is shown including a processing component 222 (e.g., one or more processors), a storage component 224 (e.g., a storage hierarchy), an input/output (I/O) component 226A (e.g., one or more I/O interfaces and/or devices), and a communications pathway 228. In general, the processing component 222 executes program code, such as the analysis program 230, which is at least partially fixed in the storage component 224. While executing program code, the processing component 222 can process data, which can result in reading and/or writing transformed data from/to the storage component 224 and/or the I/O component 226A for further processing.

The pathway 228 provides a communications link between each of the components in the computer system 220. The I/O component 226A and/or the external interface I/O component 226B can comprise one or more human I/O devices, which enable a human user 102 to interact with the computer system 220 and/or one or more communications devices to enable a system user 102 to communicate with the computer system 220 using any type of communications link. To this extent, during execution by the computer system 220, the analysis program 230 can manage a set of interfaces (e.g., graphical user interface(s), application program interface, and/or the like) that enable human and/or system users 102 to interact with the analysis program 230. Furthermore, the analysis program 230 can manage (e.g., store, retrieve, create, manipulate, organize, present, etc.) the data, such as the object data 240, using any solution.

In any event, the computer system 220 can comprise one or more general purpose computing articles of manufacture (e.g., computing devices) capable of executing program code, such as the analysis program 230, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 230 can be embodied as any combination of system software and/or application software.

Furthermore, the analysis program 230 can be implemented using a set of modules 232. In this case, a module 232 can enable the computer system 220 to perform a set of tasks used by the analysis program 230, and can be separately developed and/or implemented apart from other portions of the analysis program 230. When the computer system 220 comprises multiple computing devices, each computing device can have only a portion of the analysis program 230 fixed thereon (e.g., one or more modules 232). However, it is understood that the computer system 220 and the analysis program 230 are only representative of various possible equivalent monitoring and/or control systems that may perform a process described herein with regard to the control unit, the ultraviolet radiation sources and the sensors. To this extent, in other embodiments, the functionality provided by the computer system 220 and the analysis program 230 can be at least partially implemented by one or more computing devices that include any combination of general and/or specific purpose hardware with or without program code.

In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the disinfecting pad. Illustrative aspects of the invention are further described in conjunction with the computer system 220. However, it is understood that the functionality described in conjunction therewith can be implemented by any type of monitoring and/or control system.

Regardless, when the computer system 220 includes multiple computing devices, the computing devices can communicate over any type of communications link. Furthermore, while performing a process described herein, the computer system 220 can communicate with one or more other computer systems, such as the user 102, using any type of communications link. In either case, the communications link can comprise any combination of various types of wired and/or wireless links; comprise any combination of one or more types of networks; and/or utilize any combination of various types of transmission techniques and protocols.

Some or all of the components depicted in FIG. 2 can receive power from a power source 140. The power source 140 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power source can include solar, a mechanical energy to electrical energy converter such as a rechargeable device, etc.

In an embodiment, the control unit 122 can detect changes imparted to the object 12 from the set of radiation sources 114, 116 as a function of data determined by the set of sensors 120. In particular, the control unit 122 can detect the changes as a function of the data associated with the irradiation by the set of UV-C sources 114 and the blue-UV sources 116, and the data associated with environmental conditions surrounding the object 112. In one embodiment, the data associated with the irradiation can include the frequency, intensity, dosage, duration, and wavelength from the radiation emitted by the set of UV-C sources 116 and the blue-UV sources 118. In an embodiment, when sterilizing the surface of the object 112, the changes that can be detected by the set of sensors 120 can include change in color, change in fluorescence from the surface, change in reflective properties of the surface, and/or the like.

In an embodiment, the object 112 can be a living organism, such as a person or an animal, and the system 100 can be used to apply a medical treatment. The illuminator 110 can include an environmental device 130 that detects a set of environmental conditions that can include various vital signs such as, blood pressure, heart rate, temperature, pulse, humidity of the skin, reflectivity of the skin, and/or the like. The changes that can be detected by the control unit 122 can include, but are not limited to, color changes of the human/animal skin, visual changes occurring over the surface of the human/animal skin (e.g., curing of the wounds, changes in the scarring tissue), and/or the like.

The control unit 122 can detect the changes imparted to the object 112 from the data obtained from the set of sensors 120 using any solution. For example, in an embodiment, the set of sensors 120 can include a visual camera that is sensitive to visible radiation and the illuminator can include a third set of radiation sources 118 (FIG. 1) that includes a source of visible radiation. The visual camera can acquire image data of the object 112 at a first instance of time and at a later instance of time under similar visible radiation conditions, assuming that the surface is not moved or otherwise physically altered. The control unit 122 can compare the image data to determine changes in color, surface optical properties, and/or the like. The changes in color can provide information regarding an overall microbial growth. In an embodiment, the set of sensors 120 could also include a fluorescent detector to determine the presence of a fluorescent signal from the object 112. The third set of radiation sources 118 (FIG. 1) can include fluorescent radiation sources and the set of sensors 120 can include a fluorescence sensor in order to acquire information regarding changes of the surface related to accumulation of fluorescent bacteria. Similar to the visual source and camera, the fluorescent sources and sensors can acquire data at set instances of time, which the control unit 122 can compare at such different instances.

In one embodiment, the control unit 122 can also include a wireless transmitter and receiver that is configured to communicate with a remote location via Wi-Fi, BLUETOOTH, and/or the like. As used herein, a remote location is a location that is apart from the system 100. For example, a remote computer can be used to transmit operational instructions to the wireless transmitter and receiver. The operational instructions can be used to program functions performed and managed by the control unit 122. In another embodiment, the wireless transmitter and receiver can transmit data calculations (e.g., changes), data from the sensors to the remote computer, to facilitate further use of the system 100 with the object 112.

Figure 3A:
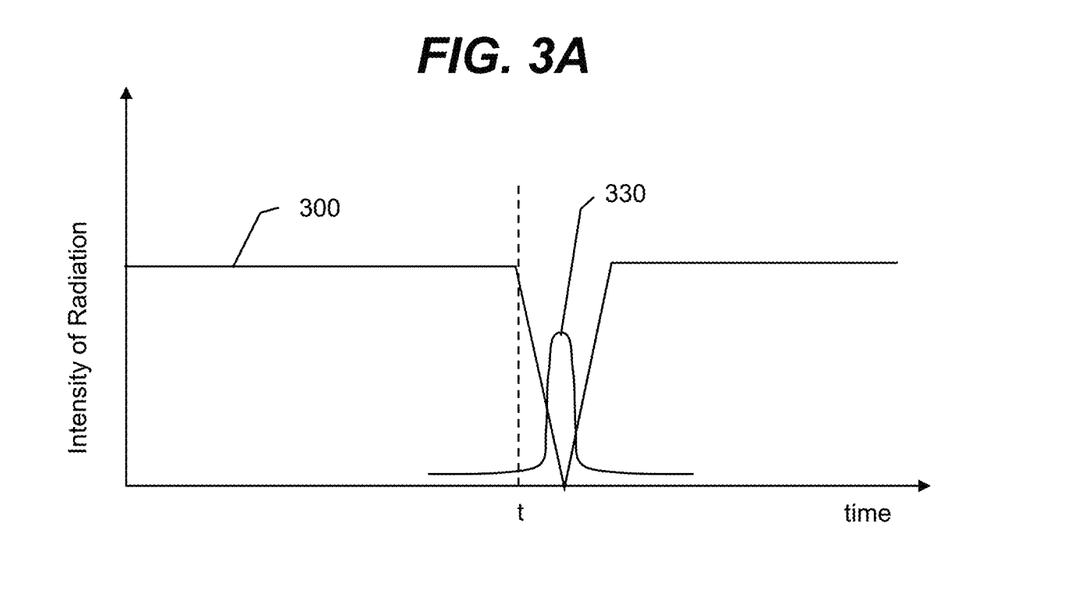
FIGS. 3A-3B show graphical examples depicting the operation of an illuminator according to an embodiment.
Figure 3B:
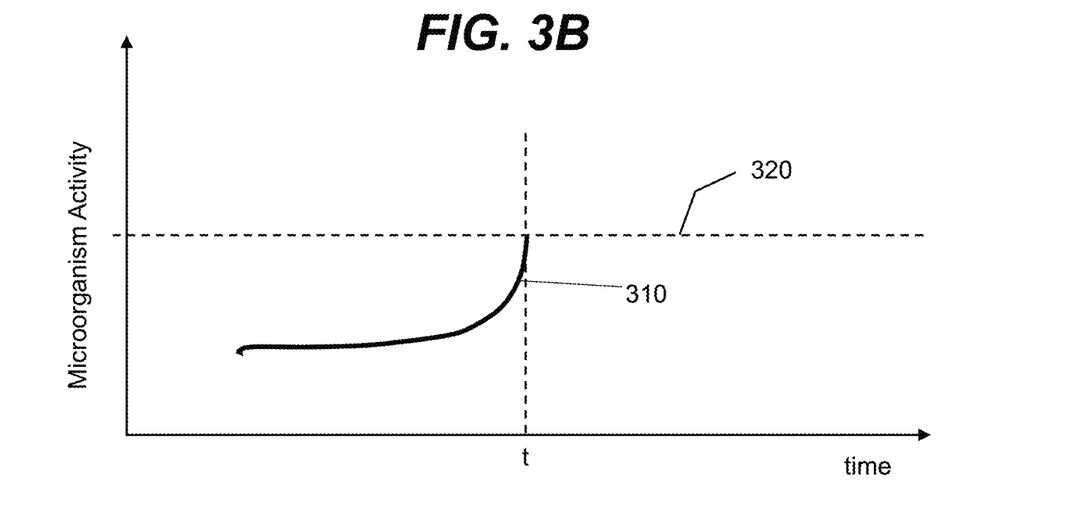

Turning now to FIGS. 3A and 3B, graphical representations that depict the operation of a scenario in which a first set of radiation sources and a second set of radiation sources, such as the first set of radiation sources 14 and the second set of radiation sources 16 shown in the embodiment shown in FIG. 1, are operated as a function of time. As shown in FIG. 3A, at section 300 of the graph, ultraviolet radiation from the second set of the radiation sources (e.g., blue-UV radiation) is used while determining whether there is any contamination of the object (e.g., based on an amplitude of a fluorescent signal sensed by a fluorescent sensor, visual data from a visual camera, and/or the like). For example, the object can be irradiated with a radiation source that is capable of eliciting a fluorescent signal if microbial activity is present. The amplitude of the fluorescent signal can indicate the level of contamination and/or the amount of microbial activity. The object can be irradiated by blue-UV radiation over a prolonged period of time that ranges from tens of minutes to tens of hours while determining whether there is a fluorescent signal. During this time, the control unit and the fluorescence sensor operate in conjunction to monitor the amount of contamination present on the surface of the object.

In this example, FIG. 3B shows a sharp increase in the growth of microorganism activity as noted by reference element 310. When the level of microorganism activity approaches a predetermined contamination threshold 320 at time t that is indicative of a need for more intense ultraviolet irradiation treatment due to rapid growth of microbial activity, then the control unit will direct the first set of ultraviolet radiation sources (e.g., UV-C radiation) to perform the more intense ultraviolet irradiation treatment at the short burst of intensity that lasts at most a few minutes (FIG. 3A, reference number 330) starting at or shortly after time t. In this manner, ultraviolet radiation (e.g., UV-C radiation) applied from the first set of ultraviolet radiation sources can bring microbial activity within appropriate limits by rapidly suppressing microbial activity on the surface of the object. The blue-UV radiation from the second set of radiation sources is used to maintain microbial activity within limits over an extended period of time, while the UV-C radiation from the first set of radiation sources is designed to rapidly suppress microbial activity.

Figure 4:
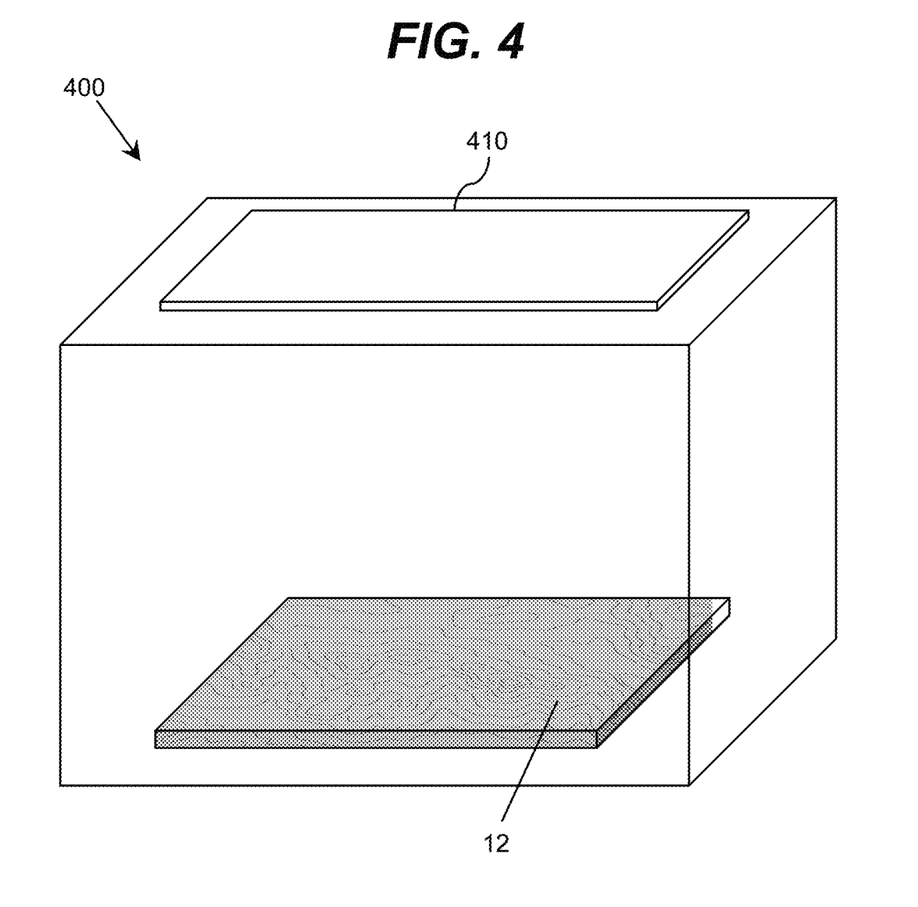
FIG. 4 shows an illustrative enclosure including an illuminator according to an embodiment.

Turning now to FIG. 4, an illustrative enclosure 400 including an illuminator 410 according to an embodiment is shown. Although the enclosure 400 is shown as a box, it is understood that the enclosure 400 can by any shape and size. The interior of the enclosure 400 can include UV reflective and/or UV diffusively reflective materials, which are used to recycle the ultraviolet radiation within the enclosure 400. An embodiment of a diffusive ultraviolet reflective layer comprises a coating or thin film of a fluoropolymer. Examples of a fluoropolymer that are suitable as a diffusive ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like. Other examples of ultraviolet material that can be used to recycle radiation can include, but are not limited to, polished aluminum, Bragg reflective dielectric mirrors, omni-directional mirrors comprising dielectric and metallic layers (e.g., aluminum), and/or the like.

In an embodiment, reflective surfaces can be combined with partially UV transparent surfaces designed for further reflection, recycling and light guiding UV radiation. In an embodiment, such surfaces can comprise UV partially transparent material such as fluoropolymers, $Al_2O_3$, sapphire, $SiO_2$, $CaF_2$, $MgF_2$, and/or the like. In this case, a surface can be formed of a partially UV transparent layer located on the interior side of the surface and a reflective layer located adjacent to the partially UV transparent layer on the exterior side of the surface. The object 12 to be disinfected is located within the enclosure 400. In an embodiment, the illuminator 410 is located on a side of the enclosure 400 that is opposite of the side that the object 12 is located. Although it is not shown, the enclosure 400 can include an additional enclosure located therein designed for producing a hydroxyl group using ultraviolet radiation, a photo-catalyst (e.g., $TiO_2$), water vapor, and/or the like, wherein the hydroxyl group is used to further disinfect the object 12.

As used herein, the singular forms "a," "an," and "the" include the plural forms as well, unless the context clearly indicates otherwise. Additionally, the terms "comprises," "includes," "has," and related forms of each, when used in this specification, specify the presence of stated features, but do not preclude the presence or addition of one or more other features and/or groups thereof.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An illuminator, comprising:
a first set of ultraviolet radiation sources, wherein each ultraviolet radiation source in the first set of ultraviolet radiation sources emits germicidally-effective ultraviolet radiation;
a second set of ultraviolet radiation sources, each ultraviolet radiation source in the second set of ultraviolet radiation sources operating in a wavelength range of approximately 380 nanometers to approximately 420 nanometers; and
a control system configured to control and adjust a set of radiation settings for the first and the second set of ultraviolet radiation sources to irradiate at least one surface of an object, wherein the control system operates the second set of ultraviolet radiation sources to irradiate the at least one surface of the object over time to determine a presence of microbial activity and the control system operates the first set of ultraviolet radiation sources to rapidly suppress microbial activity on the at least one surface of the object only when the presence of microbial activity is over a predetermined contamination threshold.

2. The illuminator of claim 1, wherein the control system controls and adjusts the set of radiation settings based on at least one attribute of the object.

3. The illuminator of claim 1, wherein the control system operates the second set of ultraviolet radiation sources in response to determining that microorganism activity is approaching a predetermined contamination threshold by reducing an intensity of the second set of ultraviolet radiation sources while increasing an intensity of the first set of ultraviolet radiation sources.

4. The illuminator of claim 1, wherein the control system continuously irradiates the at least one surface of the object using the second set of ultraviolet radiation sources for periods of time lasting at least ten minutes, and wherein the control system irradiates the at least one surface of the object using the first set of ultraviolet radiation sources for periods of time of at most three minutes.

5. The illuminator of claim 1, further comprising a set of sensors for acquiring data regarding the object to be irradiated by the first and the second set of ultraviolet radiation sources, wherein the control system controls and adjusts the set of radiation settings for the first and the second set of ultraviolet radiation sources based on the data acquired by the set of sensors.

6. The illuminator of claim 5, further comprising a radiation source configured to irradiate the at least one surface of the object with radiation capable of eliciting a fluorescent signal, wherein the set of sensors includes at least one fluorescent detector.

7. The illuminator of claim 1, further comprising an input system configured to allow a user to interact with the control system to manually control the set of radiation settings.

8. The illuminator of claim 1, wherein the control system only irradiates the at least one surface of the object using at most one of: the first set of ultraviolet radiation sources or the second set of ultraviolet radiation sources at a time.

9. The illuminator of claim 1, further comprising a third set of radiation sources, wherein the third set of radiation sources includes at least one infrared radiation source, and wherein the control system is further configured to control and adjust a set of radiation settings for the third set of radiation sources to selectively irradiate the at least one surface of the object.

10. A system for illuminating an object, comprising:
an illuminator configured to direct ultraviolet radiation at at least one surface of the object, the illuminator comprising:
a first set of ultraviolet radiation sources, wherein each ultraviolet radiation source in the first set of ultraviolet radiation sources emits germicidally-effective ultraviolet radiation;
a second set of ultraviolet radiation sources, each ultraviolet radiation source in the second set of ultraviolet radiation sources operating in a wavelength range of approximately 380 nanometers to approximately 420 nanometers;
a control system configured to control and adjust a set of radiation settings for the first and the second set of ultraviolet radiation sources to irradiate the at least one surface of the object, wherein the control system operates the second set of ultraviolet radiation sources to irradiate the at least one surface of the object over time to determine a presence of microbial activity and the control system operates the first set of ultraviolet radiation sources to rapidly suppress microbial activity on the at least one surface of the object only when the presence of microbial activity is over a predetermined contamination threshold; and an external interface component configured to provide data for use by a user and/or receive data provided by the user.

11. The system of claim 10, wherein the control system controls and adjusts the set of radiation settings based on at least one attribute of the object.

12. The system of claim 10, wherein the control system operates the second set of ultraviolet radiation sources in response to determining that microorganism activity is approaching a predetermined contamination threshold by reducing an intensity of the second set of ultraviolet radiation sources while increasing an intensity of the first set of ultraviolet radiation sources.

13. The system of claim 10, further comprising a set of sensors for acquiring data regarding the object to be irradiated by the first and the second set of ultraviolet radiation sources, wherein the control system controls and adjusts the set of radiation settings for the first and the second set of ultraviolet radiation sources based on the data acquired by the set of sensors.

14. The system of claim 13, further comprising a radiation source configured to irradiate the at least one surface of the object with radiation capable of eliciting a fluorescent signal, wherein the set of sensors includes at least one fluorescent detector.

15. The system of claim 10, further comprising a third set of radiation sources, wherein the third set of radiation sources includes at least one infrared radiation source, and wherein the control system is further configured to control and adjust a set of radiation settings for the third set of radiation sources to selectively irradiate the at least one surface of the object.

16. The system of claim 10, further comprising at least one environmental device configured to acquire data regarding a set of environmental conditions of the object.

17. A system for treating an object, the system comprising:
a structure for enclosing the object to be treated;
an illuminator configured to direct ultraviolet radiation onto the enclosed object, the illuminator comprising:
a first set of ultraviolet radiation sources, wherein each ultraviolet radiation source in the first set of ultraviolet radiation sources emits germicidally-effective ultraviolet radiation;
a second set of ultraviolet radiation sources, each ultraviolet radiation source in the second set of ultraviolet radiation sources operating in a wavelength range of approximately 380 nanometers to approximately 420 nanometers; and
a control system configured to control and adjust a set of radiation settings for the first and the second set of ultraviolet radiation sources to irradiate at least one surface of the object, wherein the control system operates the second set of ultraviolet radiation sources to irradiate the at least one surface of the object over time to determine a presence of microbial activity and the control system operates the first set of ultraviolet radiation sources to rapidly suppress microbial activity on the at least one surface of the object only when the presence of microbial activity is over a predetermined contamination threshold.

18. The system of claim 17, further comprising a set of sensors for acquiring data regarding the object to be irradiated by the first and the second set of ultraviolet radiation sources, wherein the control system controls and adjusts the set of radiation settings for the first and the second set of ultraviolet radiation sources based on the data acquired by the set of sensors.

19. The system of claim 17, further comprising an additional enclosure located within the enclosure, wherein the additional enclosure is configured to produce a hydroxyl group to disinfect the at least one object.

20. The system of claim 17, further comprising at least one environmental device configured to acquire data regarding a set of environmental conditions of the object.

21. The system of claim 17, further comprising a third set of radiation sources, wherein the third set of radiation sources includes at least one infrared radiation source, and wherein the control system is further configured to control and adjust a set of radiation settings for the third set of radiation sources to selectively irradiate the at least one surface of the object.

* * * * *